(12) United States Patent
Greggs

(10) Patent No.: US 8,969,431 B2
(45) Date of Patent: Mar. 3, 2015

(54) STABILIZING CERAMIC RESTORATIONS

(71) Applicant: Thomas S. Greggs, Wilton, CT (US)

(72) Inventor: Thomas S. Greggs, Wilton, CT (US)

( * ) Notice: Subject to any disclaimer, the term of this patent is extended or adjusted under 35 U.S.C. 154(b) by 0 days.

(21) Appl. No.: 13/948,275

(22) Filed: Jul. 23, 2013

(65) Prior Publication Data

US 2014/0030678 A1    Jan. 30, 2014

Related U.S. Application Data

(60) Provisional application No. 61/675,557, filed on Jul. 25, 2012.

(51) Int. Cl.
| | | |
|---|---|---|
| *A61C 5/08* | (2006.01) | |
| *A61K 6/093* | (2006.01) | |
| *A61K 6/00* | (2006.01) | |
| *A61C 5/00* | (2006.01) | |

(52) U.S. Cl.
CPC .............. *A61K 6/093* (2013.01); *A61K 6/0023* (2013.01); *A61K 6/0073* (2013.01); *A61K 6/0094* (2013.01); *A61C 5/00* (2013.01); *A61C 5/08* (2013.01)
USPC .................. 523/118; 433/288.1; 523/116

(58) Field of Classification Search
None
See application file for complete search history.

(56) References Cited

U.S. PATENT DOCUMENTS

| | | | | | |
|---|---|---|---|---|---|
| 2,938,009 | A | * | 5/1960 | Lucas | 523/212 |
| 3,024,126 | A | * | 3/1962 | Brown | 106/490 |
| 3,159,601 | A | * | 12/1964 | Ashby | 528/15 |
| 3,436,366 | A | * | 4/1969 | Modic | 524/862 |
| 3,445,420 | A | * | 5/1969 | Kookootsedes et al. | 524/862 |
| 3,635,743 | A | * | 1/1972 | Smith | 106/490 |
| 3,715,334 | A | * | 2/1973 | Karstedt | 528/15 |
| 3,847,848 | A | * | 11/1974 | Beers | 523/213 |
| 3,884,866 | A | * | 5/1975 | Jeram et al. | 523/203 |
| 3,957,713 | A | * | 5/1976 | Jeram et al. | 524/703 |
| 4,041,010 | A | * | 8/1977 | Jeram | 524/16 |
| 4,162,243 | A | * | 7/1979 | Lee et al. | 524/847 |
| 4,256,870 | A | * | 3/1981 | Eckberg | 528/15 |
| 4,427,801 | A | * | 1/1984 | Sweet | 523/212 |
| 4,529,752 | A | * | 7/1985 | Bluestein | 523/214 |
| 4,599,374 | A | * | 7/1986 | Bluestein | 523/213 |
| 4,762,859 | A | * | 8/1988 | Modic et al. | 521/82 |
| 4,871,782 | A | * | 10/1989 | Modic et al. | 521/88 |
| 4,954,533 | A | * | 9/1990 | Modic et al. | 521/82 |
| 5,036,117 | A | * | 7/1991 | Chung et al. | 522/172 |
| 5,674,966 | A | * | 10/1997 | McDermott et al. | 528/32 |
| 5,863,965 | A | * | 1/1999 | Hare | 523/109 |
| 7,090,498 | B2 | | 8/2006 | Engelbrecht | |
| 7,998,264 | B2 | | 8/2011 | Lubbers et al. | |
| 2009/0247663 | A1 | | 10/2009 | Kamohara et al. | |
| 2012/0095109 | A1 | * | 4/2012 | Garaud et al. | 514/772.3 |

FOREIGN PATENT DOCUMENTS

WO    2006045646 A    5/2006

OTHER PUBLICATIONS

Coltene Whaledent, Temposil 2 product literature, 2012.
GC America Inc., Fit Checker—Base MSDS, Feb. 20, 2012.
GC America Inc., Fit Checker Advanced—Base MSDS, Aug. 3, 2011.
GC America Inc., Fit Checker Advanced—Catalyst MSDS, Aug. 3, 2011.
GC America Inc., Fit Checker Catalyst MSDS, Feb. 20, 2012.
GC America Inc., Fit Checker II—Base MSDS, Feb. 20, 2012.
GC America Inc., Fit Checker II—Catalyst MSDS, Feb. 21, 2012.
GC America Inc., Fit Checker Retarder MSDS, Mar. 8, 2010.
Troendle, G.R.; Troendle, K.B.; Cavazos, E "Film thickness of four diclosing media" J.Prosthetic Dentistry, 1991, 65/6, 856-857.
US FDA, Temposil 2 501K determination, Feb. 6, 2009.

* cited by examiner

*Primary Examiner* — James J Seidleck
*Assistant Examiner* — Peter A Salamon
(74) *Attorney, Agent, or Firm* — Synthesis Intellectual Property, LLC

(57) ABSTRACT

An adhesive adapted for stabilizing ceramic restorations for dental use, that includes a reaction product of an admixture of: a di(organo)polysiloxane that includes at least two vinylic groups and has a viscosity of at least 100 cP at 25° C.; a silicone resin; an (organo)(hydrogen)polysiloxane; a silanated fumed silica; and a filler. Preferably, the admixture includes a di(organo)polysiloxane that includes at least two vinylic groups and has a viscosity of at least 100 cP at 25° C.; a silicone resin; an (organo)(hydrogen)polysiloxane; an organoplatinum polymerization catalyst; a silanated fumed silica; a polymerization retardant; an inorganic pigment; and a filler.

11 Claims, No Drawings

STABILIZING CERAMIC RESTORATIONS

CROSS-REFERENCE TO RELATED APPLICATIONS

This disclosure claims the benefit of priority to U.S. Provisional Patent Application No. 61/675,557 filed 25 Jul. 2012 which is incorporated herein in its entirety.

FIELD OF THE INVENTION

This invention is directed to the composition, formation and use of a dental adhesive for the short-term adhesion of a dental form (e.g., a ceramic restoration) to a support (e.g., a tooth or a mold).

BACKGROUND

Dental crown restorations traditionally have been fabricated from precious metals and alloys, porcelain fused to metal, and to a smaller degree, all-ceramic or porcelain. Materials used for dental crown restorations have changed over the past 10 years. To date, 20% of all dental crown restorations are fabricated with all-ceramic materials—and this market is growing.

Porcelain veneer restorations are also fabricated with all-ceramic materials and have steadily grown in popularity in the last twenty years. For the purpose of definition, porcelain veneers, all-ceramic crowns, or dental restorations fabricated from porcelain, ceramic or ceramic-like materials are referred to as all-ceramic dental restorations. All-ceramic dental restorations are made upon the order of a dentist by a dental laboratory technician.

The dentist takes a dental impression of the teeth to be restored. The dental impression is then filled with dental stone to fabricate a stone model that replicates the tooth or teeth to be restored. Typically, at this stage, the stone working model is used by the dental laboratory technician to begin the necessary steps to fabricate the all-ceramic dental restoration to fit the prepared tooth or teeth. The stone model is deemed the "working model"; the working model is sectioned into individual working dies to replicate the tooth or teeth to be restored. Dental ceramic material is milled or pressed into the designated shape based upon the working dies, and is subsequently finished and contoured to fit on the working dental model.

During final fabrication of all-ceramic restorations, a 30-50 micron space or gap exists between the all-ceramic restoration and the working stone die. This gap replicates the space that will be occupied by a cement, luting, or bonding material when the restoration is permanently adhered to the tooth in the mouth. In comparison, the fabrication process for all-metal or porcelain-fused-to-metal dental crown restorations yields a more intimate fit of approximately 20 microns to the working stone die on the working models, and subsequently the prepared tooth. Thus, the fit of all-ceramic restorations differs from that of metal or porcelain-fused to metal restorations in that the all-ceramic restoration fits the working stone die, and subsequently the prepared tooth, with a larger space of 30-50 microns. A problem arises in the final finishing and contouring stage of all-ceramic crown fabrication due to the 30-50 micron space between the all-ceramic restoration and the working die. Due to the 30-50 micron gap, the all-ceramic restorations fall off of their respective dies during the finishing and contouring process and it is difficult to keep them in place on the working dies in order to complete the finishing and contouring procedure. This same problem exists when the dentist places the all-ceramic restorations on the prepared teeth in the mouth during the process of evaluating external contour and color, making any re-contouring adjustments and/or polishing before final cementation, luting or bonding of the restorations to the teeth.

Since the inception of all-ceramic restorations, many methods have been tried to keep the all-ceramic restorations temporarily secured to their respective working dies on the working model during finishing and contouring in the dental laboratory setting. Materials that have been used to temporarily adhere the all-ceramic restoration to the die often stick to the restoration and contaminate the ceramic and/or it is time consuming to remove these materials from the all-ceramic restoration and the working stone die.

Additionally, in the dental office setting, it is common practice to make use of a water-soluble try-in paste that allows the dentist and patient to judge what the final color of the all-ceramic restoration will look like before it is permanently adhered to the tooth. The try-in paste is tooth-colored and incapable of adhering to the tooth surface or the all-ceramic restoration. Typically, the color of the try-in paste matches the color of the cement or luting material that will be used to permanently adhere the all-ceramic restoration to the prepared tooth. For nearly twenty years try-in pastes have been available from several companies in the dental market. The primary problem with use of the try-in paste is that the paste will marginally hold the all-ceramic restoration in place on the prepared tooth for only a very limited amount of time, making it difficult to assess color and fit before the restorations dislodge, which increases the risk of breakage before they are permanently adhered to the prepared tooth.

SUMMARY

A first embodiment is an adhesive adapted for dental use, that includes a reaction product of an admixture of: a di(organo)polysiloxane that includes at least two vinylic groups and has a viscosity of at least 100 cP at 25° C.; a silicone resin; an (organo)(hydrogen)polysiloxane; a silanated fumed silica; and a filler. Preferably, the admixture includes a di(organo)polysiloxane that includes at least two vinylic groups and has a viscosity of at least 100 cP at 25° C.; a silicone resin; an (organo)(hydrogen)polysiloxane; an organoplatinum polymerization catalyst; a silanated fumed silica; a polymerization retardant; an inorganic pigment; and a filler.

Another embodiment is a kit for the preparation of the herein described adhesive; the kit preferably includes two admixtures, a first admixture that includes the (organo)(hydrogen)polysiloxane and a second admixture that includes the hydrosilation catalyst (e.g., the organoplatinum polymerization catalyst).

Still another embodiment is a process of adhering a dental form (e.g., an all-ceramic restoration) to a support (e.g., a tooth in mouth or a die for further external contouring and/or color assessment) using the herein described adhesive medium with tooth-like optical properties.

DETAILED DESCRIPTION

An object of the present invention to provide a product and method to adhere all-ceramic restorations to the dental stone dies, and/or prepared teeth, and also to easily retrieve, remove and handle the adhered dental forms and adhesive.

A first embodiment is an adhesive adapted for dental use. The adhesive includes a reaction product of an admixture of: a di(organo)polysiloxane that includes at least two vinylic groups and has a viscosity of at least 100 cP at 25° C.; a silicone resin; an (organo)(hydrogen)polysiloxane; a silanated fumed silica; and a filler. Preferably, the admixture includes a di(organo)polysiloxane that includes at least two vinylic groups and has a viscosity of at least 100 cP at 25° C.; a silicone resin; an (organo)(hydrogen)polysiloxane; an organoplatinum polymerization catalyst; a silanated fumed silica; a polymerization retardant; an inorganic pigment; and a filler.

In an example, the admixture which reacts to form the adhesive includes about 55 wt. % to about 80 wt. %; preferably about 60 wt. % to about 75 wt. %; more preferably about 65 wt. % to about 70 wt. % of the di(organo)polysiloxane. The di(organo)polysiloxane is preferably a vinyl terminated polysiloxane, more preferably a vinyl terminated dimethylpolysiloxane. The di(organo)polysiloxane can have a viscosity of at least 100 cP at 25° C.; more preferably the di(organo) polysiloxane has a viscosity greater than about 100 cP, greater than about 200 cP, greater than about 250 cP, greater than about 500 cP, greater than about 750 cP, greater than about 1,000 cP, greater than about 5,000 cP, or greater than about 10,000 cP. As used herein and unless otherwise designated, all viscosities are the viscosity of the respective material at 25° C.

The admixture can include about 1 wt. % to about 25 wt. %; preferably about 5 wt. % to about 20 wt. %; more preferably about 10 wt. % to about 15 wt. % of the silicone resin. In one preferable example, the silicone resin is a vinyl Q resin. In another preferable example the silicone resin has a CAS number of 68584-83-8. In another example, the silicone resin is a hydrolysis product of sodium silicate with chlorotrimethylsilane and dichloroethenylmethylsilane. The silicon resin can be a dispersion in a solvent.

Still further, the admixture can include about 1 wt. % to about 20 wt. %; preferably about 2 wt. % to about 15 wt. %; more preferably about 3 wt. % to about 10 wt. %; even more preferably about 4 wt. % to about 5 wt. % of the (organo) (hydrogen)polysiloxane. The (organo)(hydrogen)polysiloxane can be a hydrogen terminated polysiloxane (i.e., has Si—H functionality at the ends of the polymer chain) or can be a methyl terminated polysiloxane that has Si—H functionality in the backbone of the polymer. The (organo)(hydrogen) polysiloxane can be a hydrogen terminated dimethylpolysiloxane (i.e., the polymer has Si—H functionality at the ends of a polymer chain that primarily includes —(Si(CH$_3$)$_2$O)— repeat units); preferably, the (organo)(hydrogen)polysiloxane is a (methyl)(hydrogen) terminated dimethylpolysiloxane (i.e., the ends of the polymer chain comprise —OSi(CH$_3$) H).

The reaction of the admixture to form the adhesive is promoted by the inclusion of a polymerization catalyst in the admixture. Preferably, the polymerization catalyst is a hydrosilation catalyst (i.e., the catalyst promotes to addition of a Si—H to a terminal alkene). One preferable polymerization catalyst is an organoplatinum polymerization catalyst, for example a Pt(0) catalyst. The organoplatinum polymerization catalyst can be selected from the group consisting of the Karstedt's catalyst, a platinum chloride olefin complex, and a platinum olefin complex. Specific examples of catalysts include Pt$_2${[(H$_2$C=CH)(Me)$_2$Si]$_2$O}$_3$, PtCl$_2$(1,5-octadiene), Pt(1,5-octadiene)$_2$) and mixtures thereof. Other hydrosilylation catalyst include, but should not be limited to, PtO$_2$, H$_2$PtCl$_6$, Rh(cod)$_2$BF$_4$, [Rh(nbd)Cl]$_2$, Rh(PPh$_3$)$_3$Cl, [Ru($\eta^6$-arene)Cl$_2$]$_2$, Cp*Ru(NCMe)$_3$PF$_6$, and Ru(PPh$_3$)$_2$Cl$_2$ (CHPh).

Silanated fumed silica can be included in the admixture in an amount of about 1 wt. % to about 25 wt. %; preferably about 2 wt. % to about 10 wt. %; more preferably about 3 wt. % to about 5 wt. % of a silanated fumed silica.

The admixture further can include a polymerization retardant. The polymerization retardant can be a polysiloxane having vinyl groups on proximal silicone atoms, for example, 2,4,6,8-Tetramethyl-2,4,6,8-tetravinylcyclotetrasiloxane. Preferably, the admixture includes less than about 0.1 wt. %, less than about 0.075 wt. %, or less than about 0.05 wt. % of the polymerization retardant.

Still further, the admixture can include an inorganic pigment that permits a user to distinguish between the adhesive and a dental form. The admixture can include about 0.1 wt. % to about 5 wt. %; preferably 0.1 wt. % to about 2.5 wt. %; more preferably about 0.1 wt. % to about 1 wt. % of the inorganic pigment. Preferably, the inorganic pigment has a maximum particle diameter less than about 100 μm, less than about 50 μm, less than about 10 μm, less than about 5 μm, less than about 1 μm, or less than about 0.5 μm. In one example, the inorganic pigment can be a phyllosilicate, preferably, wherein the phyllosilicate comprises a mica. Even more preferably, the inorganic pigment includes (preferably, consists essentially of (i.e., the inorganic pigment does not include other pigments or colorants) a micronized mica (i.e. a mica with a particle size of less than about 50 microns, preferably less than about 44 microns (e.g., a mica that can pass through a 325 mesh screen), more preferably less than about 40 microns).

Importantly, the admixture (and the resultant adhesive) includes a filler. The filler is included in the admixture in an amount less than about 25 wt. %, preferably less than 20 wt. %, more preferably less than 15 wt. %. For example, the admixture can include about 1 wt. % to about 25 wt. %; preferably about 5 wt. % to about 20 wt. %; more preferably about 10 wt. % to about 15 wt. % of the filler. In one example, the filler is selected from the group consisting of calcium carbonate, diatomaceous earth, calcium silicate, ground silica, dolomite, magnesium silicate, and a mixture thereof. Preferably, the filler has a maximum particle diameter less than about 100 μm, less than about 50 μm, less than about 10 μm, less than about 5 μm, less than about 1 μm, or less than about 0.5 μm.

In another example, the adhesive that is the reaction product of the admixture has a Shore A hardness value of about 20 to about 50, preferably about 25 to about 45, more preferably about 30 to about 35 as measured by ASTM D2240.

In another embodiment, the adhesive adapted for dental use, includes a Shore A hardness of about 25 to about 35; and a reaction product of an admixture that comprises: about 55 wt. % to about 80 wt. % of a di(organo)polysiloxane that includes at least two vinylic groups; about 1 wt. % to about 25 wt. % of a silicone resin; about 1 wt. % to about 20 wt. % of an (organo)(hydrogen)polysiloxane; an organoplatinum polymerization catalyst; about 1 wt. % to about 15 wt. % of a silanated fumed silica; and a polymerization retardant. Preferably, the admixture further includes about 0.1 wt. % to about 5 wt. % of the inorganic pigment; preferably, the admixture further includes about 1 wt. % to about 25 wt. % of the filler.

Another embodiment is a kit for the preparation of the herein described adhesive. The kit preferably includes two admixtures, a first admixture that includes the (organo)(hydrogen)polysiloxane and a second admixture that includes the hydrosilation catalyst (e.g., the organoplatinum polymerization catalyst). While the compositions of the first mixture and the second mixture can vary, one important distinction is the separation of the hydrosilanes (e.g., the (organo)(hydrogen)polysiloxane) and the hydrosilation catalyst. In one example the first admixture includes about 55 wt. % to about 80 wt. % of the di(organo)polysiloxane that includes at least two vinylic groups and has a viscosity of at least 100 cP at 25° C.; about 1 wt. % to about 25 wt. % of the silicone resin; about 1 wt. % to about 20 wt. % of the (organo)(hydrogen)polysiloxane; about 1 wt. % to about 15 wt. % of the silanated fumed silica; about 0.1 wt. % to about 5 wt. % of the inorganic pigment; and about 1 wt. % to about 25 wt. % of the filler. In this example, the second admixture includes about 55 wt. % to about 80 wt. % of the di(organo)polysiloxane that includes at least two vinylic groups and has a viscosity of at least 100 cP at 25° C.; about 1 wt. % to about 25 wt. % of the silicone resin; about 0.01 wt. % to about 0.5 wt. % of the organoplatinum polymerization catalyst; about 1 wt. % to about 15 wt. % of the silanated fumed silica; about 0.01 wt. % to about 0.1 wt. % of the polymerization retardant; and about 1 wt. % to about 25 wt. % of the filler. Even more preferably, the kit can further include an extruder tube fluidly connected to a first volume that contains the first admixture and a second volume that contains the second admixture. Preferably, the extruder tube is adapted to mix the first admixture and the second admixture as the first admixture and the second admixture are drawn from the respective volumes.

Still another embodiment is a process of adhering a dental form to a support using the herein described adhesive. This process can include admixing the first admixture which includes: about 55 wt. % to about 80 wt. % of the di(organo)polysiloxane that includes at least two vinylic groups and has a viscosity of at least 100 cP at 25° C.; about 1 wt. % to about 25 wt. % of the silicone resin; about 1 wt. % to about 20 wt. % of the (organo)(hydrogen)polysiloxane; about 1 wt. % to about 15 wt. % of the silanated fumed silica; about 0.1 wt. % to about 5 wt. % of the inorganic pigment; and about 1 wt. % to about 25 wt. % of the filler and the second admixture which includes: about 55 wt. % to about 80 wt. % of the di(organo)polysiloxane that includes at least two vinylic groups and has a viscosity of at least 100 cP at 25° C.; about 1 wt. % to about 25 wt. % of the silicone resin; about 0.01 wt. % to about 0.5 wt. % of the organoplatinum polymerization catalyst; about 1 wt. % to about 15 wt. % of the silanated fumed silica; about 0.01 wt. % to about 0.1 wt. % of the polymerization retardant; and about 1 wt. % to about 25 wt. % of the filler to form the adhesive; then applying the adhesive to either the dental form or the support; positioning the dental form against the support with the adhesive there between; and then curing the adhesive. Preferably the adhesive is cured to a Shore A hardness value of about 25 to about 35. More preferably, the dental form is positioned against the support with about 30 to about 50 microns of adhesive there between.

What is claimed:

1. A dental adhesive consisting of a reaction product of an admixture that comprises:
   about 55 wt. % to about 80 wt. % of a di(organo)polysiloxane that includes at least two vinylic groups and has a viscosity of at least 100 cP at 25° C.;
   about 1 wt. % to about 25 wt. % of a silicone resin;
   about 1 wt. % to about 20 wt. % of an (organo)(hydrogen)polysiloxane;
   an organoplatinum polymerization catalyst;
   about 1 wt. % to about 25 wt. % of a silanated fumed silica;
   a polymerization retardant;
   about 0.1 wt. % to about 5 wt. % of a micronized mica having a particle size less than about 40 microns; and
   about 1 wt. % to about 25 wt. % of a filler selected from the group consisting of calcium carbonate, diatomaceous earth, calcium silicate, ground silica, dolomite, magnesium silicate, and a mixture thereof; where the filler has a maximum particle diameter less than about 10 μm;
   wherein the dental adhesive has a Shore A hardness value of about 25 to 35;
   wherein the dental adhesive has tooth-like optical properties and wherein the mica distinguishes optically the dental adhesive from a dental form.

2. The adhesive of claim 1, wherein the di(organo)polysiloxane is a vinyl terminated dimethylpolysiloxane that has a viscosity greater than about 100 cP at 25° C.

3. The adhesive of claim 1, wherein the silicone resin is a vinyl Q resin.

4. The adhesive of claim 3, wherein the silicone resin is a hydrolysis product of sodium silicate with chlorotrimethylsilane and dichloroethenylmethylsilane.

5. The adhesive of claim 1, wherein the (organo)(hydrogen)polysiloxane is a (methyl)(hydrogen) terminated dimethylpolysiloxane.

6. The adhesive of claim 1, wherein the organoplatinum polymerization catalyst is selected from the group consisting of Karstedt catalyst, a platinum chloride olefin complex, and a platinum olefin complex, preferably selected from the group consisting of $Pt_2\{[(H_2C\!\!=\!\!CH)(Me)_2Si]_2O\}_3$, $PtCl_2(1,5$-octadiene), $Pt(1,5$-octadiene$)_2$) and a mixture thereof.

7. The adhesive of claim 1, wherein the polymerization retardant is a polysiloxane having vinyl groups on proximal silicone atoms.

8. The adhesive of claim 1, wherein the dental adhesive includes 0.1 wt. % to about 1 wt. % of the mica.

9. A dental adhesive comprising:
   a cured polysiloxane that includes 0.1 wt. % to 5 wt. % of a micronized mica and 10 wt. % to 15 wt. % of a filler selected from the group consisting of calcium carbonate, diatomaceous earth, calcium silicate, ground silica, dolomite, magnesium silicate, and a mixture thereof; where the filler has a maximum particle diameter less than about 10 μm;
   the dental adhesive having a Shore A hardness value of about 25 to about 35.

10. A kit for the preparation of an adhesive that is adapted for dental use, the kit comprising:
   a first admixture that includes: about 55 wt. % to about 80 wt. % of a di(organo)polysiloxane that includes at least two vinylic groups and has a viscosity of at least 100 cP at 25° C.; about 1 wt. % to about 25 wt. % of a silicone resin; about 1 wt. % to about 20 wt. % of an (organo)(hydrogen)polysiloxane; about 1 wt. % to about 25 wt. % of a silanated fumed silica; about 0.1 wt. % to about 5 wt. % of an micronized mica having a particle size less than about 40 microns; and about 1 wt. % to about 25 wt. % of a filler selected from the group consisting of calcium carbonate, diatomaceous earth, calcium silicate, ground silica, dolomite, magnesium silicate, and a mixture thereof; where the filler has a maximum particle diameter less than about 10 μm; and
   a second admixture that includes: about 55 wt. % to about 80 wt. % of a di(organo)polysiloxane that includes at least two vinylic groups and has a viscosity of at least 100 cP at 25° C.; about 1 wt. % to about 25 wt. % of a silicone resin; about 0.01 wt. % to about 0.5 wt. % of an organoplatinum polymerization catalyst; about 1 wt. % to about 15 wt. % of a silanated fumed silica; about 0.01 wt. % to about 0.1 wt. % of a polymerization retardant; and about 1 wt. % to about 25 wt. % of a filler selected from the group consisting of calcium carbonate, diatomaceous earth, calcium silicate, ground silica, dolomite, magnesium silicate, and a mixture thereof; where the filler has a maximum particle diameter less than about 10 μm.

11. The kit of claim 10 further comprising an extruder tube fluidly connected to a first volume that contains the first admixture and a second volume that contains the second admixture.

* * * * *